United States Patent
Giambattista et al.

(10) Patent No.: US 6,793,646 B1
(45) Date of Patent: Sep. 21, 2004

(54) PEN STYLE INJECTOR WITH AUTOMATED SUBSTANCE COMBINING FEATURE

(75) Inventors: Lucio Giambattista, East Hanover, NJ (US); David DeSalvo, Butler, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/958,125

(22) PCT Filed: Apr. 6, 2000

(86) PCT No.: PCT/US00/09135

§ 371 (c)(1),
(2), (4) Date: Jan. 18, 2002

(87) PCT Pub. No.: WO00/62839

PCT Pub. Date: Oct. 26, 2000

Related U.S. Application Data

(60) Provisional application No. 60/129,796, filed on Apr. 16, 1999.

(51) Int. Cl.[7] .......................... A61M 37/00; A61M 5/00
(52) U.S. Cl. .......................... 604/90; 604/92; 604/232; 604/208
(58) Field of Search .......................... 604/82–92, 56, 604/224, 232, 234, 511, 208

(56) References Cited

U.S. PATENT DOCUMENTS

| | | | |
|---|---|---|---|
| 4,202,314 A | * | 5/1980 | Smirnov et al. ............ 604/138 |
| 4,755,169 A | * | 7/1988 | Sarnoff et al. ............ 604/511 |
| 4,822,340 A | | 4/1989 | Kamstra ............ 604/135 |
| 4,874,381 A | | 10/1989 | Vetter ............ 604/191 |
| 4,929,230 A | | 5/1990 | Pfleger ............ 604/90 |
| 4,968,299 A | | 11/1990 | Ahlstrand et al. ............ 604/90 |
| 5,267,963 A | * | 12/1993 | Bachynsky ............ 604/134 |
| 5,290,228 A | | 3/1994 | Uemura et al. ............ 604/90 |
| 5,536,249 A | | 7/1996 | Castellano et al. ............ 604/65 |
| 5,713,857 A | | 2/1998 | Grimard et al. ............ 604/82 |
| 5,865,798 A | | 2/1999 | Grimard et al. ............ 604/89 |
| 5,971,953 A | * | 10/1999 | Bachynsky ............ 604/90 |
| 6,277,097 B1 | * | 8/2001 | Mikkelsen et al. ............ 604/187 |
| 6,368,306 B1 | * | 4/2002 | Koska ............ 604/218 |

FOREIGN PATENT DOCUMENTS

| WO | 0062839 | 10/2000 |
|---|---|---|

* cited by examiner

Primary Examiner—Michael J. Hayes
(74) Attorney, Agent, or Firm—David M. Fortunato; Hoffmann & Baron LLP

(57) ABSTRACT

A pen-style injector (20) includes an automated mover (70) that completes a combination of two substances such as a reconstitution process to reconstitute a lyophilized medicament prior to making an injection. The automated mover (70) is preloaded selectively released to automatically reconstitute the medicament at a controlled rate. The illustrated embodiment includes a mechanical spring (70) that provides the necessary movement of components within the injector (20) to complete the automated reconstitution process. The injector also has safety features (100) to prevent an injection prior to completing the automated combination of the substances.

20 Claims, 5 Drawing Sheets

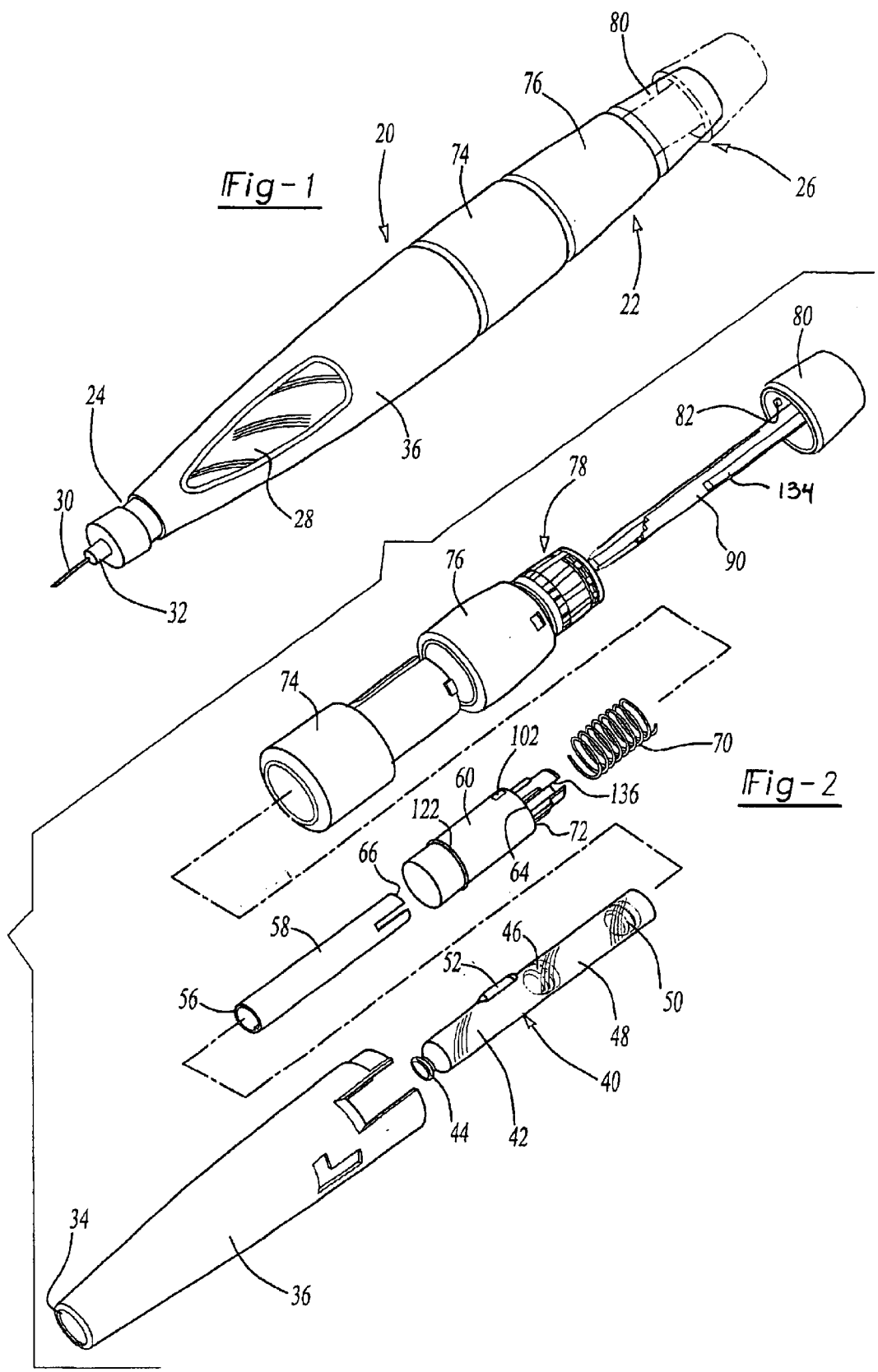

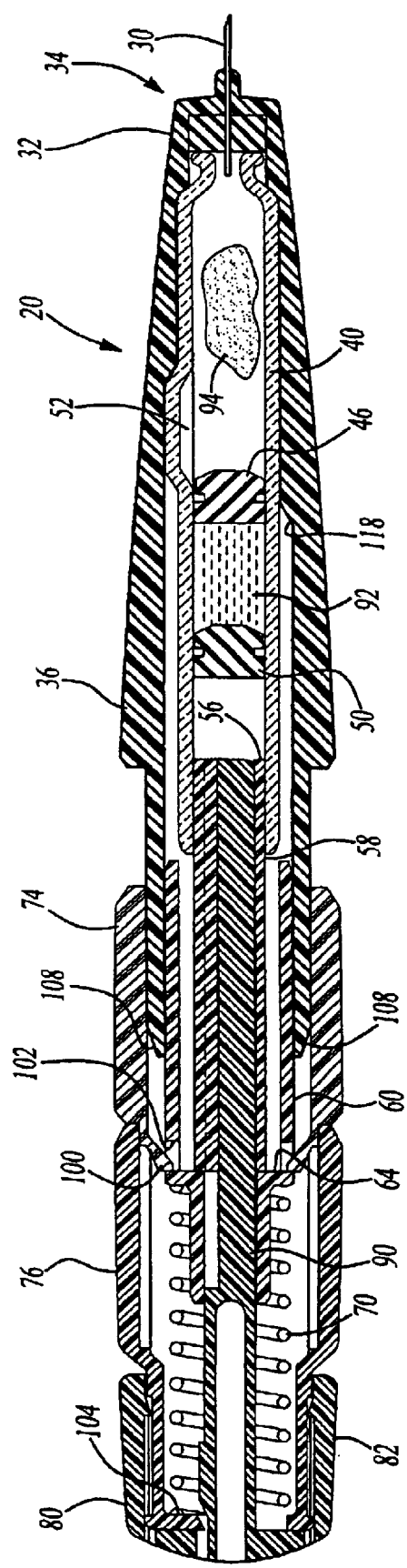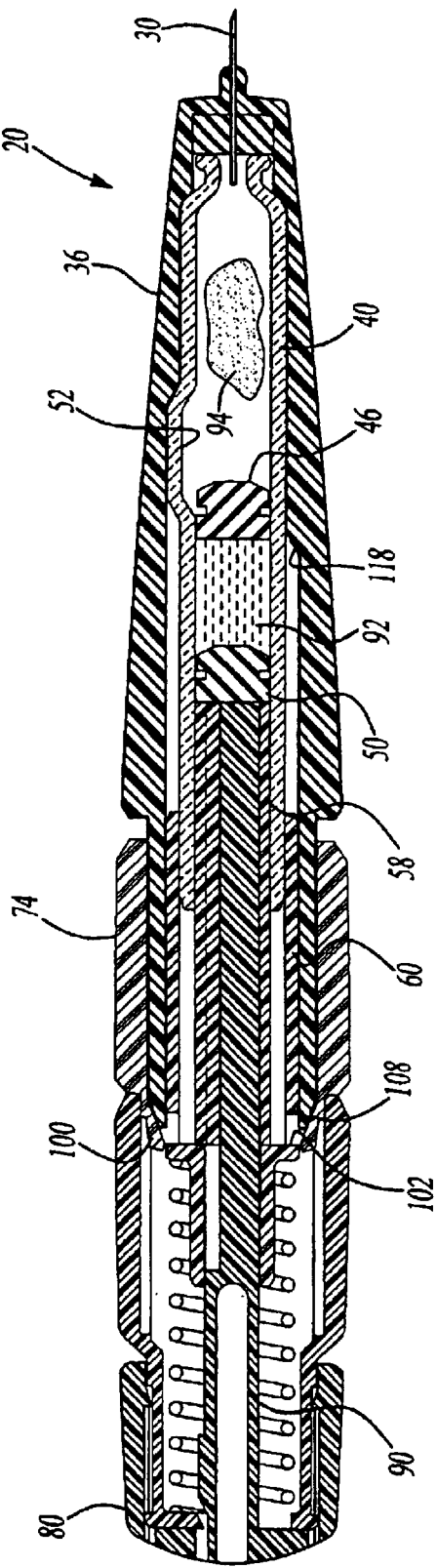

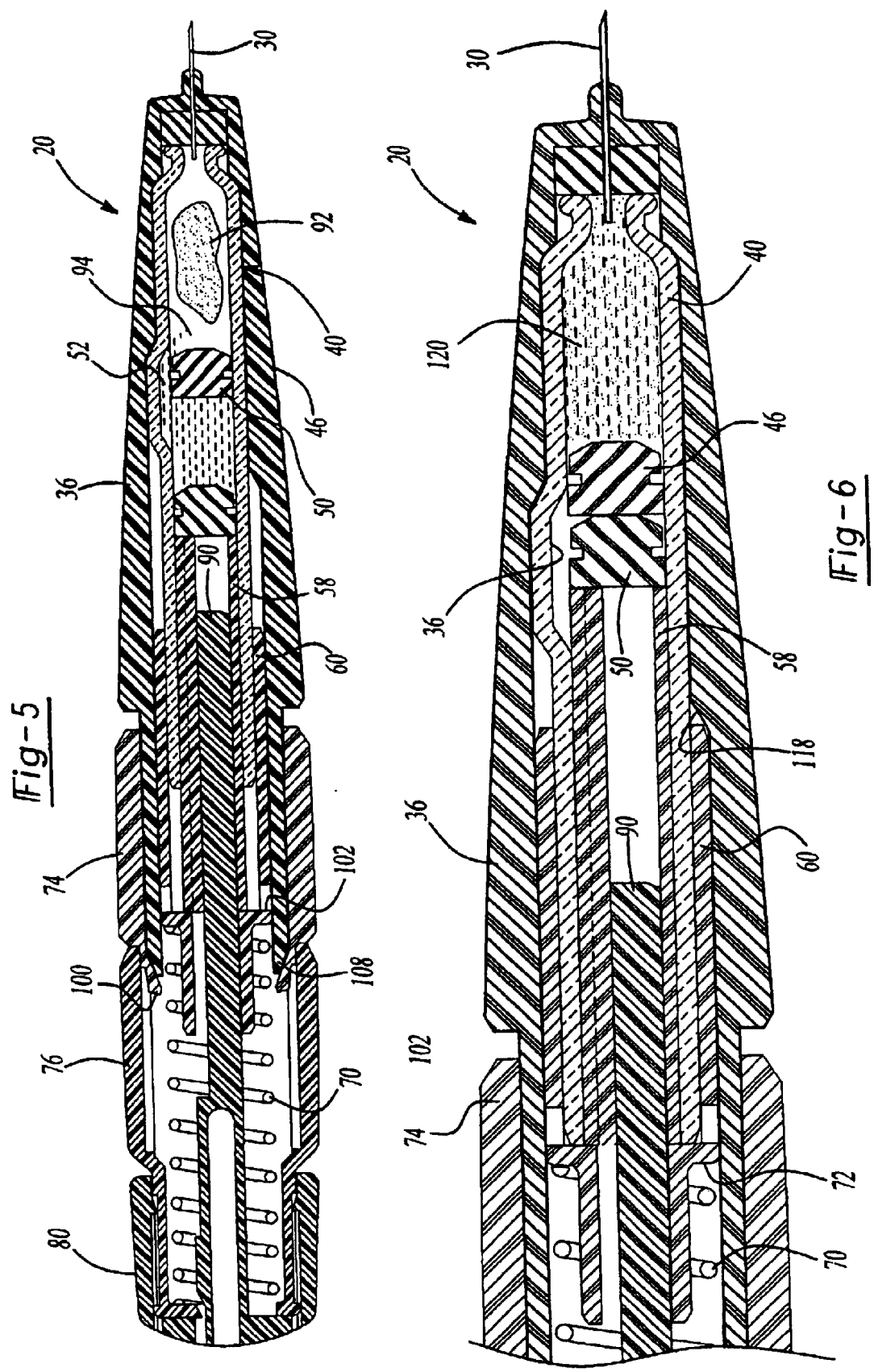

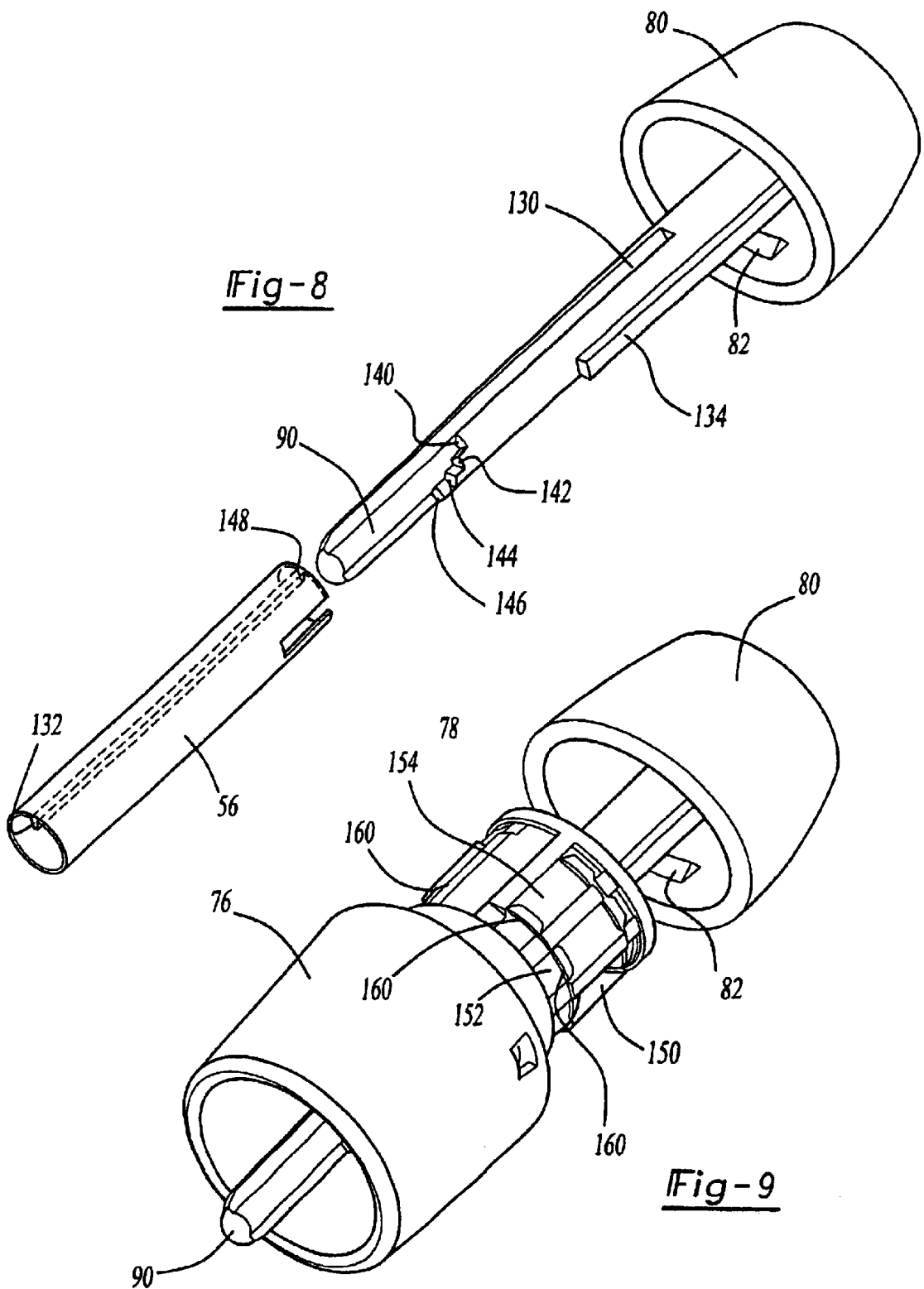

PEN STYLE INJECTOR WITH AUTOMATED SUBSTANCE COMBINING FEATURE

This application claims the benefit of provisional application No. 60/129,796, filed Apr. 16, 1999.

BACKGROUND OF THE INVENTION

In general terms, this invention relates to pen style injectors, more particularly, this invention relates to a pen style injector having an automated feature for combining at least two substances such as reconstituting a lyophilized medicament prior to performing an injection.

A wide variety of syringes and injectors are commercially available. One type of injector that is popular is sometimes referred to a pen style injector because the injector body resembles a writing pen. Pen injectors have proven convenient in a wide variety of applications.

One difficulty associated with using conventional pen style injectors occurs when the drug or medicament that is to be administered is provided in a lyophilized form. Lyophilized substances typically are supplied in a freeze-dried form that needs to be mixed with a liquid to reconstitute the substance into a form that is suitable for making an injection. Other substances that require reconstitution are provided in powder form. Under some circumstances, the reconstitution procedure must be performed carefully and at a controlled rate to ensure appropriate reconstitution.

The problem with conventional injectors is that they are dependent upon manual activation to complete a reconstitution procedure. The individual typically has to rotate different portions of the injector relative to each other using a screw-type action to move components within the injector to complete a reconstitution process. Examples of such devices are shown in U.S. Pat. No. 4,874,381 issued to Vetter, and U.S. Pat. No. 4,968,299 issued to Ahlstrand et al., the teachings of each being incorporated by reference into this specification. In other designs relative axial movements are used to accomplish the reconstitution. Such procedures can prove difficult for some individuals and potentially introduce ergonomic concerns.

Moreover, manual reconstitution procedures typically cannot be performed at a consistently controlled rate. Certain lyophilized substances require reconstitution at a controlled rate to ensure that the lyophilized substance is appropriately reconstituted. For example, some medicaments will foam up if the reconstituting liquid is introduced too quickly. A foamed medicament is typically not suitable for injection and, therefore, manual reconstitution procedures present the possibility for requiring an extended waiting period before administering a particular dosage. Additionally, there may be uncertainty regarding whether the substance is ready for making an injection.

Another potential problem associated with manually activated pen style injectors is that the reconstitution process may not be performed completely. Without appropriate controls, under some circumstances, its possible for an individual to fail to completely reconstitute the lyophilized or powder-form medicament. Under such circumstances, the incompletely reconstituted medicament may have a reduced or ineffective efficacy.

This invention provides an improved pen style injector that avoids the shortcomings and drawbacks discussed above. An injector designed according to this invention includes an automated combining or reconstitution feature that is not dependent upon manual operation and consistently provides a controlled combination or reconstitution rate.

SUMMARY OF THE INVENTION

In general terms, this invention is an injector device that is useful for combining multiple substances prior to performing an injection with the same device. An injector designed according to this invention includes a body and a substance retaining portion. The preferred retaining portion has at least a first chamber and a second chamber with a communication passage between the two chambers. The first chamber contains a first substance such as a lyophilized medicament while the second chamber contains a second substance such as liquid for reconstituting the lyophilized medicament. The injector device includes an automated mover that automatically moves the second substance from the second chamber through the communication passage and into the first chamber to automatically combine the substance prior to injecting the substances into a patient.

The currently preferred embodiment includes a mechanical spring that is preloaded within the body. When the mechanical spring is released the physical force provided by the spring automatically moves appropriate components within the injector to complete the combination or reconstitution process in an automated fashion.

The preferred embodiment not only automatically combines at least two substances but also automatically primes the injector for an injection. The automated mover preferably ensures that the substances are combined automatically and that any air bubbles within the combined substances are expelled from the injector.

Another feature of the preferred embodiment is a safety locking mechanism that prevents premature activation of the injector prior to appropriately mixing the substances within the retainer portion. The components of the injector preferably are designed such that a trigger or button for performing an injection cannot be moved go until after the components that effect the desired mixing of the substances have moved into position indicating that the mixing is complete. Cooperating grooves and ribs on the components of the injector preferably prevent the injection trigger from being moved into a position where an injection becomes possible until after the automated mixing has been completed.

The various features and advantages of this invention will become apparent to those skilled in the art from the following detailed description of the currently preferred embodiment. The drawings that accompany the detailed description can be briefly described as follows.

BRIEF DESCRIPTION OF THE DRAWINGS

FIG. 1 is a diagrammatic illustration of an injector designed according to this invention.

FIG. 2 is a perspective, exploded view of the embodiment of FIG. 1.

FIG. 3 is a cross sectional view showing the embodiment of FIG. 1 in a first condition.

FIG. 4 illustrates the embodiment of FIG. 1 after two portions of the injector body have been manually moved relative to each other.

FIG. 5 is a cross-sectional illustration showing the beginning of the automatic reconstitution process.

FIG. 6 is a partial cross-sectional illustration showing selected portions of the embodiment of FIGS. 1–5 at the completion of the automated reconstitution process.

FIG. 8 is a perspective illustration of selected components of the embodiment of FIG. 1.

FIG. 9 is a perspective illustration of selected components of the embodiment of FIG. 1.

DETAILED DESCRIPTION OF THE PREFERRED EMBODIMENT

Figure 7:
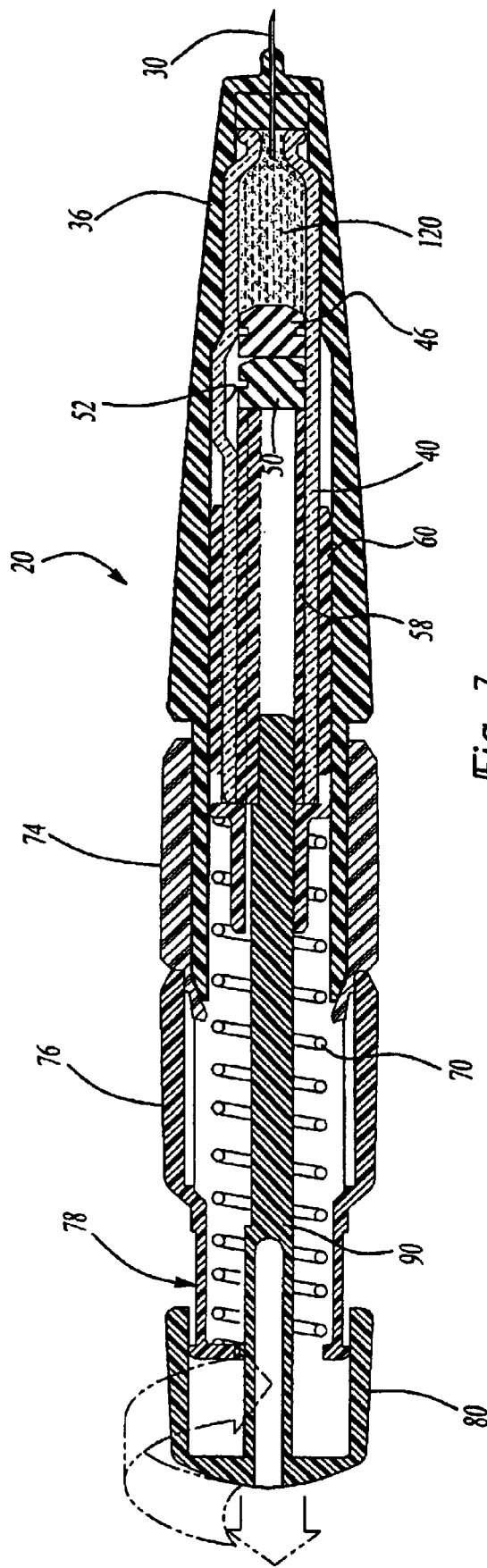
FIG. 7 is a cross-sectional illustration showing another operational feature where the injector is being set to make an injection after the automated reconstitution process has been completed.

FIGS. 1 and 2 diagrammatically illustrate a pen style injector 20 having a body 22 that is adapted to fit within an individual's hand. The injector 20 includes a proximal, front or forward end 24 and a distal, back or rear end 26. A viewing window 28 allows an individual to see the contents of the injector before or after an injection. In the illustrated example, the injector 20 is used to perform a hypodermic injection using a needle 30. This invention is not limited, however, to such hypodermic injectors but also can be used, for example, in needleless injectors.

This specification refers to "proximal," "forward" or "front" interchangeably and "distal," "rear" or "back" interchangeably to refer to directions or ends of various components. Those terms are used for illustration and discussion purposes only. The particular arrangement of components and their directions of movement contained in the illustrated example are not to be construed in a limiting sense.

The illustrated injector 20 includes the needle 30 and an adapter 32 that are fitted onto a forward end 34 of a body portion 36. The needle 30 and adapter 32 may take a variety of forms depending on the needs of a particular situation. Alternatively, the needle may be supported entirely by structure that is integrally formed as part of the body portion 36. The body portion 36 preferably is a generally elongate, cylindrical housing that is made from a plastic material.

The body portion 36 includes a substance retainer portion 40. In the illustrated example, separate cartridge is the substance retainer 40, which is received within and supported by the body portion 36. The cartridge 40 preferably is made from glass or clear plastic material as is known in the art. A first chamber 42 is defined between a forward end 44 of the cartridge 40 and a first stopper member 46. The first chamber 42 preferably contains a first substance such as a lyophilized medicament in dry form such as alpha interferon for treating hepatitis including hepatitis C.

A second chamber 48 is defined between the first stopper member 46 and a second stopper member 50. The second chamber 48 preferably includes a second substance such as a liquid for reconstituting the lyophilized medicament. The first and second chambers can be in communication through a communication passage, for example. The communication passage in the cartridge 40 includes a communication channel 52 formed in the side wall that allows selective communication between the first chamber 42 and the second chamber 48 so that the two substances can be combined as needed. For purposes of illustrations, the following discussion will describe a reconstitution of a lyophilized medicament. Other mixing or combining operations are possible.

It is important to note that, although a separate cartridge is illustrated as the example retainer portion 40, other configurations are within the scope of this invention. For example, the retainer portion can be integrally formed with or made as a part of the body portion 36. Additionally, the communication passage 52 is illustrated as a portion of the cartridge. Alternative communication passages can be utilized including specially designed stoppers or valve mechanisms. Example stoppers are shown in U.S. Pat. No. 5,713, 857 issued to Grimard et al.; and U.S. Pat. No. 4,929,230 issued to Pfleger. The teachings of each of those patents are incorporated by reference into the specification. Additionally, although only a first chamber 42 and second chamber 48 are shown in the illustrated example, more than two separate chambers within the substance retaining portion 40 can be utilized as shown in U.S. Pat. No. 5,865,798 issued to Grimard et al. depending on the needs of a particular situation.

In operation, the second stopper 50 is moved through the interior of the cartridge 40 as it is contacted by a forward end 56 of a plunger or engaging member 58. A sleeve 60 preferably is generally cylindrical and has an opening at a front edge 62 through which the plunger 58 is received. The sleeve 60 includes an interior surface 64 that abuts against a rear portion 66 of the plunger 58 so that forward movement of the sleeve 60 results in simultaneous forward movement of the plunger 58 as will be described below.

The injector 20 includes an automated mover 70 for automatically moving the sleeve 60 and the plunger 58 in a manner to automatically reconstitute the lyophilized drug contained in the cartridge 40. Since the mover 70 acts on the sleeve 60 and the latter acts on the plunger 58. During the automated reconstitution process, the sleeve 60 serves as a reconstituting intermediary member. The currently preferred embodiment includes a mechanical spring as the automated mover 70. This invention is not limited, however, to mechanical springs. Other automated movers such as gas springs, pressurized gas, electrically powered devices or a combination of them may be suitable under certain circumstances.

The mover 70 preferably is received against a surface 72 on the sleeve 60. The sleeve 60 and the mover 70 preferably are received within a generally cylindrical body portion, which is illustrated having two members 74 and 76.

A rear end 78 of the body portion member 76 receives and cooperates with a button or knob 80, which is used to complete an injection as will be described below. The knob 80 preferably includes a tab or projection 82 that cooperates with one or more grooves on the end 78 of the body portion 76 to control when an injection is possible and to control dosage as will be described below. The injector trigger or knob 80 includes an injector rod 90, which is used to perform the eventual injection as will described below.

Referring to FIG. 3, a cross-section of the injector 20 is shown. FIG. 3 shows the preferred state of the injector 20 as it would be provided to an individual user. The cartridge 40 contains a liquid substance 92 in the second chamber 48 and a lyophilized medicament 94 in the first chamber 44. The lyophilized medicament 94 must be reconstituted before an injection can be made.

In the illustrated condition, the sleeve 60 is held in place by locking tabs 100, which preferably are integrally formed as part of the body portion 74. The locking tabs 100 are received within corresponding slots 102 on the sleeve 60. In this position, the spring 70 is preloaded having ends biased against the surface 72 on the sleeve 60 and an interior surface 104 on the body portion 76.

When the individual user intends to reconstitute the medicament 94, the body portion 36 and the body portion 74 are moved axially relative to each other into the position shown in FIG. 4. A rear edge 108 on the body portion 36 engages the locking tabs 100 and moves them radially outward, removing them from the slots 102. Once the tabs 100 are removed from the slots 102, the mover 70 is free to move the sleeve 60 forward within the cartridge holder 36.

An intermediate stage is illustrated in FIG. 5 after the mover 70 has begun to discharge. As the sleeve 60 moves forward it carries with it the plunger 58 because of the interaction between the interior surface 64 on the sleeve 60 and the rear edge 66 of the plunger 58. The plunger 58 forces the second stopper member 50 in a forward direction. The fluid 92 within the second chamber 48 provides hydraulic pressure to move the first stopper member 46 in a forward direction. Eventually, the first stopper member 46 is moved into a position where the liquid 92 is able to flow through the communication channel 52 and reconstitution has begun.

Continued movement of the sleeve 60 and plunger 58 force the second stopper member 50 to continue moving forward until all of the liquid 92 is expelled from the second chamber 48. Upon completion of this portion of the process, the second stopper member 50 abuts up against the rear side of the first stopper member 46. The continued movement of the plunger 58, as caused by the mover 70, forces the two stopper members forward until at least the first stopper member 46 seals off the now reconstituted medicament 120 in the first chamber 42 as shown in FIG. 6.

The preferred embodiment includes a stop surface 118 on the interior of the body portion 36 against which the leading edge 62 of the sleeve 60 is received at the completion of the automated reconstitution process. When the leading edge 62 abuts against the stop 118, the spring 70 is no longer free to move the sleeve 60 and plunger 58. The dimensional relationships of the various components of the injector 20 preferably are designed so that the completion of the reconstitution process results in at least the first stopper member 46 sealing off the reconstituted medicament 120 within the first chamber 42 so that no back flow through the communication channel 52 is possible.

In the preferred embodiment, the automated mover 70 not only brings about automatic reconstitution of the lyophilized medicament, but also automatically primes the injector 20 to make an injection. After the medicament has been reconstituted, it is necessary to ensure that all air bubbles are removed from the first chamber 42. Accordingly, the automated mover 70 preferably causes the stopper members 50 and 46 to continue moving in a forward direction sufficiently so that any air bubbles within the reconstituted medicament 120 are expelled through the needle 30 so that the injector 20 is ready to perform an injection. Priming is best accomplished by holding the injector 20 so that the needle 30 is pointing upwards. A baffle can be incorporated onto the injector on needle assembly to capture any medicament that is expelled during the automated priming of the injector 20.

Not only does this invention provide an automated combining or reconstitution process, but it also provides the advantage of having a controlled reconstitution rate. By selecting an appropriate spring constant, component surfaces and dimensional relationships between the sleeve 60 and body portion 36, for example, the rate of movement of the fluid 92 through the communication channel 52 can be accurately controlled. The preferred embodiment includes a damper to further control the rate of movement of the components that are moved by the automated mover 70. In the illustrated embodiment, the damper includes an O-ring 122 that is received on a corresponding groove on the sleeve 60 (see FIG. 2). Alternatively, a layer of silicone or other substance may be deposited on the interior of the body portion 36 or the exterior of the sleeve 60 to provide a more controlled rate of relative movement between those components. Additionally, the materials from which the various components of the injector 20 are made can be selected to provide different glide rates, which result in different rates of relative movement between the various components. Given this description, those skilled in the art will be able to choose from among various materials and component configurations in order to achieve a desired reconstitution rate.

Once the automated reconstitution is complete, the injector 20 can be used to make an injection. Referring to FIGS. 7 through 9, the knob 80 is pulled distally (or rearward) and then rotated to set a chosen dose. An injection is completed by manually pushing the knob 80 toward the body portion 76.

The preferred embodiment includes an arrangement that prevents the injector 20 from being used to administer an injection until after the automated combination procedure is successfully complete. The injector rod or injection intermediary member, 90 preferably includes an elongated channel 130 that receives a rib 132 on the plunger 58 when the injector is assembled by the manufacturer. The rib 132 remains within the channel 130 until the reconstitution is completed and the knob is pulled rearward away from the body portion 76. The injector rod 90 most preferably includes a rib 134 that is received within a corresponding channel or slot 136 on the sleeve 60 (see FIG. 2) prior to the automated reconstitution process. The rib 134 and slot 136 cooperate to prevent the knob 80 from being rotated until the rib 134 is clear of the slot 136. When the sleeve 60 moves forward to complete the automated reconstitution and the knob 80 is moved distally, the rib 134 exits the slot 136 and the knob 80 is free to be rotated relative to the injector body.

The injector rod 90 also includes a helical arrangement of steps or abutment surfaces 140, 142, 144 and 146. Depending on the selected dosage, one of the steps will engage a rear end 148 on the rib 132 so that manual movement of the knob 80 will cause simultaneous movement of the plunger 58 in a forward direction. The plunger 58 moves the stopper members 50 and 46 forward to cause the reconstituted medicament 120 to be expelled from the tip of the needle 30 to complete a hypodermic injection.

To facilitate selecting a dosage, the end 78 of the body portion 76 preferably includes a plurality of grooves or channels 150, 152, 154. Although not all of them are visible in the view of FIG. 9, each of the channels corresponds to a respective one of the steps 140–146. The projection or tab 82 on the knob 80 preferably is aligned with and then received by a selected one of the channels so that the knob 80 can be pressed forward to make an injection. The end 78 preferably includes an arrangement of channels and annular grooves that require the knob to first be pulled backward or distally and then rotated to a selected dosage setting before the injection can be completed.

Additionally, the preferred embodiment includes a locking ridge 160 within each channel that lockingly engages the tab 82 upon completion of the injection. The interaction between the tab 82 and the ridge 160 preferably provides an audible snap so that the user can confirm that the injector rod 90 has moved forward sufficiently to deliver the desired dosage. The preferred embodiment also includes having the rib 134 bottom out on the rear end of the sleeve 60, which is biased against the stop surface 118 by the discharged mover 70. The interaction between the end of the rib 134 and the rear end of the sleeve 60 provides a physical stop at the end of an injection.

The knob 80 preferably cannot be moved in any direction after the tab 82 passes over the ridge 160 so that the injector 20 can only be used for one injection. Limiting the injector 20 to a single use is important in situations where the reconstituted medicament 120 has a limited shelf life. The currently preferred embodiment, therefore, is a disposable device that is discarded after an injection is completed.

Alternative designs are within the scope of this invention, including a reusable device or one that provides only one dosage setting. The illustrated example includes the ability to deliver various dosages and is intended to be a single-use device.

Additionally, although reconstitution of a lyophilized medicament has been described above, a pen injector designed according to this invention provides an automated combination of at least two substances for a variety of purposes. Other medicaments, such as those stored in powder form, can be reconstituted. Alternatively, different substances such as multiple vaccines, which must be stored in isolation but can be injected simultaneously, can be combined using the automated combination feature of this invention. Those skilled in the art will realize that an injector designed according to this invention is advantageous for use in a variety of circumstances.

In summary, an injector 20 designed according to this invention is used in the following manner. The injector 20 preferably is provided to the end user with the substance retaining portion containing the difference substances in the different chambers. The automated mover 70 is locked into a preloaded condition.

Just prior to use, the body portions 36 and 76 are moved relative to each other to release the locking tabs 100. At this point the automated mover 70 is free to move and automatically combine the substances in the different chambers of the retainer portion 40. After the automated combination is completed, the desired dosage can be chosen.

The knob 80 preferably is pulled in a distal direction and then rotated into a position corresponding to a desired dose. The needle 30 then is inserted into the desired location for the injection and the knob 80 is manually pressed to expel the combined substances from the injector through the needle 30 into the recipient of the injection.

The description given above provides an example embodiment of this invention. Variations and modifications may become apparent to those skilled in the art that do not necessarily depart from the basis of this invention. The scope of legal protection given to this invention can only be determined by studying the following claims.

What is claimed is:

1. An injector device for automatically combining two substances, comprising:
    a body;
    a substance retaining portion having at least a first and second chamber with selective communication between the first and second chambers, the first chamber containing a first substance and the second chamber containing a second substance to be selectively combined with the first substance, wherein the retaining portion includes a front orifice, a front stopper member, a rear stopper member and a second orifice at an end of the retaining portion that is opposite from the front orifice, the front stopper member separates the front chamber from the second chamber, and wherein the automated mover engages and moves the rear stopper member;
    an automated mover supported by the body and that automatically moves the second substance from the second chamber and into the first chamber to automatically combine the first and second substances;
    a manual trigger for expelling said combined substances from the first chamber and into a patient, said trigger being activatable only once said automated mover has combined the substances;
    a needle supported at a first end of the body to perform a hypodermic injection and wherein the retaining portion is supported within the body between the needle and the automated mover and the automated mover is supported within the body between the retaining portion and a second end of the body;
    an engaging member that engages the rear stopper and a reconstituting intermediary member that engages the engaging member responsive to a force from the automated mover such that the engaging member engages and moves the rear stopper member; and
    an injection intermediary member that engages the engaging member responsive to actuation of the trigger such that the engaging member moves the rear stopper member and the front stopper member to expel the combined substances out of the front orifice of the retaining portion.

2. The device of claim 1, wherein the automated mover includes a spring.

3. The device of claim 1, wherein the automated mover includes a mechanical spring that is preloaded within the body such that a bias of the spring urges the second substance into the first chamber.

4. The device of claim 3, wherein the spring has a preselected spring constant and the spring is preloaded a selected amount such that the substances are automatically combined at a desired rate.

5. The device of claim 1, wherein the automated mover also automatically moves any excess air out of the first chamber such that the first chamber contains only the combined substances.

6. The device of claim 1, wherein the body is generally cylindrical and has a size that is adapted to fit within an individual's hand.

7. The device of claim 1, wherein the reconstituting intermediary member has a portion that interacts with a corresponding portion of the injection intermediary member such that the reconstituting intermediary member prevents the injection intermediary member from moving the engaging member and the rear stopper member until after the reconstituting intermediary member has caused the engaging member to move the rear stopper member such that the first and second substances have been combined.

8. The device of claim 1, including a locking element that locks the trigger into a non-use position after an injection has been administered such that the device can only be used for a single injection.

9. The device of claim 1, including a dosage control adjustment that is manually adjustable among a plurality of dosage amounts such that an injection includes dispensing a selected one of the plurality of dosages.

10. The device of claim 1, wherein the engaging member is generally cylindrical having a front end that engages the rear stopper member and a rear end, the reconstituting intermediary member comprises a generally cylindrical sleeve that at least partially surrounds the engaging member and has an internal surface that abuts against the rear end of the engaging member to move the engaging member responsive to the force from the automated mover.

11. The device of claim 10, wherein the reconstituting intermediary member has a front edge and the body includes a stop surface that abuts the front edge to limit an amount of movement of the reconstituting intermediary member and the engaging member responsive to the force from the automated mover.

12. The device of claim 10, wherein the reconstituting intermediary member includes an opening adjacent the internal surface and the injection intermediary member is received through the opening such that the injection intermediary member moves the rear end of the engaging member away from the sleeve internal surface during an injection.

13. The device of claim 1, wherein the body includes a first body portion and a second body portion that is selectively moveable relative to the first body portion and including a locking mechanism that locks the automated mover into a preloaded condition and wherein movement of the second body portion relative to the first body portion releases the locking mechanism to allow the automated mover to automatically combine the substances.

14. The device of claim 13, wherein the locking mechanism includes at least one locking tab that is received within a corresponding slot and wherein axial movement of the second body portion relative to the first body portion releases the locking tab from the slot such that the automated mover is released from the preloaded condition to thereby move the liquid into the first chamber to reconstitute the medicament.

15. The device of claim 1, including a viewing window on the body near the substance retaining portion to allow visual inspection of the contents of the retaining portion.

16. The device of claim 1, wherein the first substance is a lyophilized medicament in a dry form and the second substance is a liquid for reconstituting the lyophilized medicament.

17. The device of claim 16, wherein the lyophilized medicament comprises alpha interferon.

18. The device of claim 1, including a damper that is effective to control a rate of movement of the automated mover.

19. The device of claim 1, including a communication passage between the first and second chambers.

20. The device of claim 19, wherein the communication passage is a channel formed in the retaining portion.

* * * * *